United States Patent [19]
Alter et al.

[11] Patent Number: 4,968,304
[45] Date of Patent: Nov. 6, 1990

[54] SYRINGE

[75] Inventors: Konrad G. Alter, Maylands; Jennifer D. Griffiths, West Leederville, both of Australia

[73] Assignee: Nujenko Pty Ltd., Welshpool, Australia

[21] Appl. No.: 274,204

[22] Filed: Nov. 21, 1988

[30] Foreign Application Priority Data

Oct. 20, 1988 [AU] Australia .............................. PJ1079

[51] Int. Cl.$^5$ ............................................. A61M 5/32
[52] U.S. Cl. .................................... 604/192; 604/198; 604/263
[58] Field of Search ............... 604/198, 263, 187, 110, 604/192

[56] References Cited

U.S. PATENT DOCUMENTS

| | | | |
|---|---|---|---|
| 3,134,380 | 5/1964 | Armao | 604/198 |
| 4,220,151 | 9/1980 | Whitney | 604/110 |
| 4,695,274 | 9/1987 | Fox | 604/198 |
| 4,702,738 | 10/1987 | Spencer | 604/263 X |
| 4,816,022 | 3/1989 | Poncy | 604/198 |
| 4,826,488 | 5/1989 | Nelson et al. | 604/198 |

Primary Examiner—John D. Yasko
Attorney, Agent, or Firm—Harness, Dickey & Pierce

[57] ABSTRACT

A sheath for the needle of a hypodermic syringe to isolate the needle so as to avoid contamination and injury, particularly after use of the needle. The sheath comprises a hollow body having an opening at one end and is movable relative to the syringe needle between a first position in which the syringe needle is wholly contained within the hollow body and a second position in which the syringe needle extends through the opening in the hollow body.

16 Claims, 2 Drawing Sheets

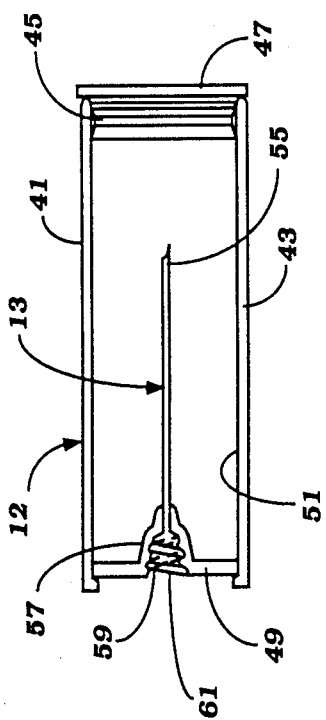
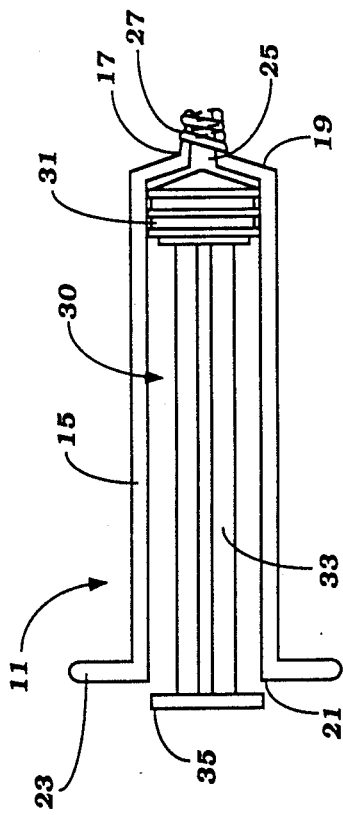
Figure 1
Figure 2

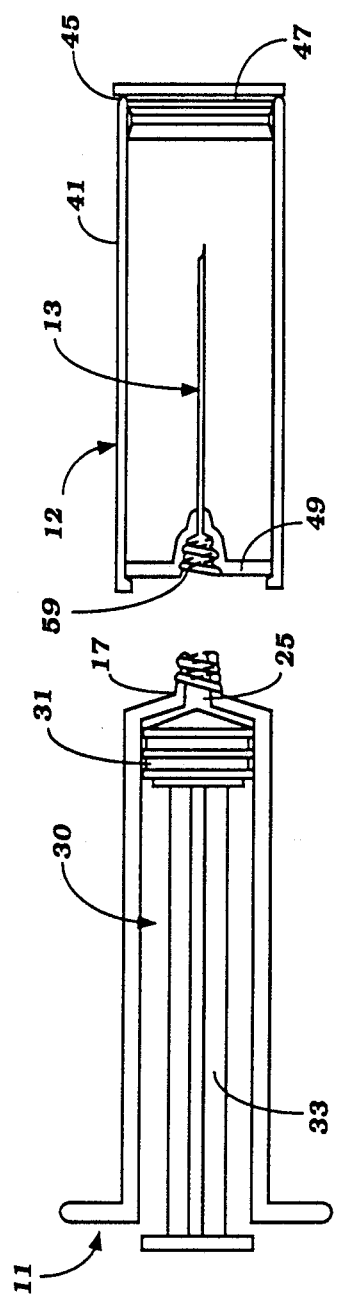
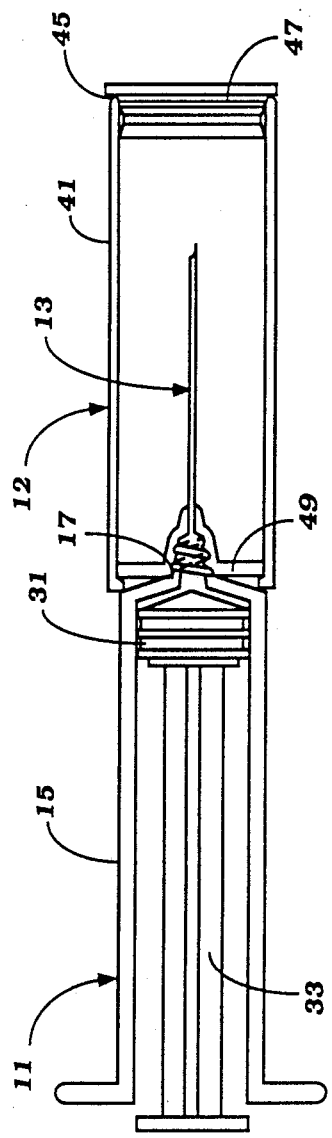
Figure 3
Figure 4

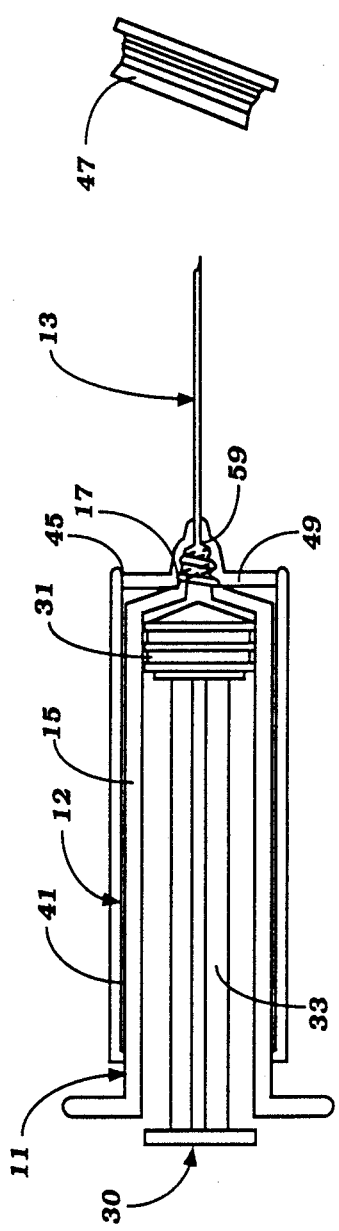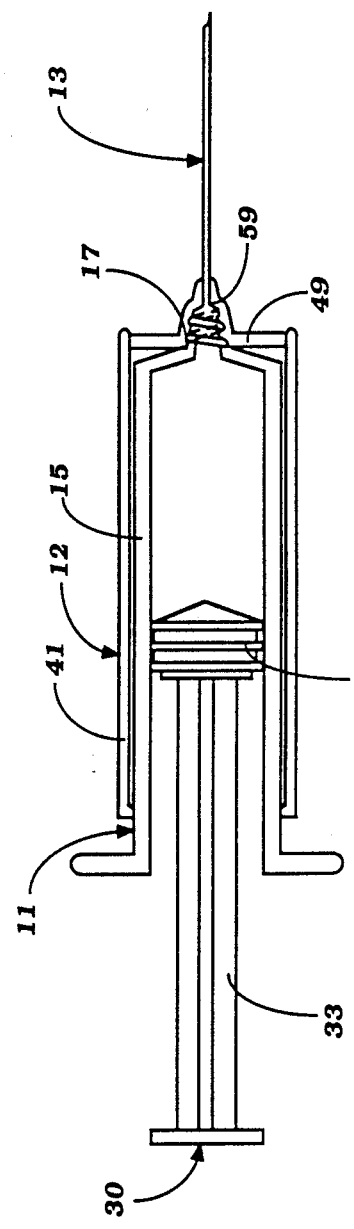

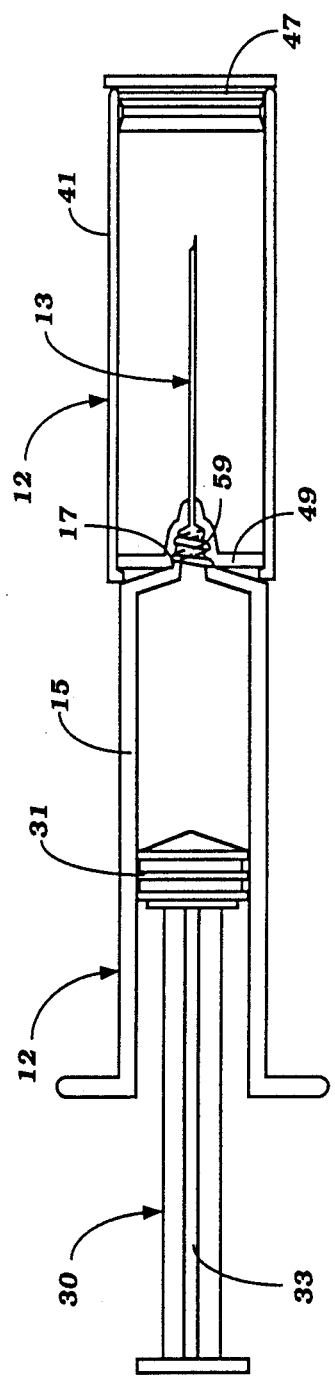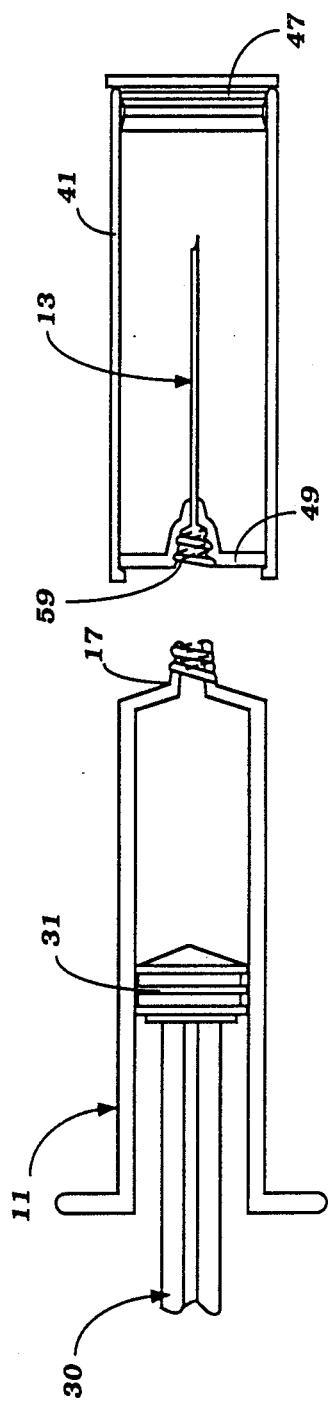
Figure 7
Figure 8

SYRINGE

BACKGROUND OF THE INVENTION

This invention relates to a protective sheath for a needle of a syringe, to a syringe for use with the protective sheath and to a combination of a syringe and a protective sheath for the needle of the syringe.

Throughout this specification, the term "syringe" shall be taken to include hypodermic syringes and other devices incorporating a needle for injection of fluid into, or extraction of fluid from, a body.

With conventional syringes, the syringe needle remains exposed after use and may cause injury or transmit infection. With a view to overcoming this problem, there have been proposals for syringes in which the syringe needle is retractable after use into the body of the syringe to isolate the needle and thereby avoid contamination and injury.

The present invention seeks to provide an alternative arrangement for isolating a syringe needle to avoid contamination and injury.

SUMMARY OF THE INVENTION

In one form the invention resides in a protective sheath for a syringe needle one end of which needle is adapted for connection to a syringe, said protective sheath comprising a hollow body having a movable wall and an opening opposite said movable wall, said movable wall being adapted to support the syringe needle with said one end exposed to the exterior of the hollow body to facilitate connection to the syringe, said wall being movable between a first position in which the needle is disposed wholly within the confines of the hollow body and a second position in which the needle extends outwardly of the hollow body through said opening.

Preferably, said one end of the needle is integral with said movable wall.

Preferably, said one end of the needle includes socket opening onto the exterior face of the said movable wall, said socket being arranged to receive and retain part of the syringe to provide fluid communication between the needle within the syringe.

Preferably, said hollow body includes side wall means one end of which defines said opening and wherein said movable wall is slidably supported between said side wall means for movement therealong between said first and second positions.

Preferably said side wall means comprises a cylindrical side wall.

Preferably, guide means are provided for guiding said movable wall as it moves along said side wall means.

Preferably, a closure means is provided for selectively closing said opening. The closure means may be in the form of a cap adapted to be removably fitted onto said one end of the cylindrical side wall.

In another form the invention resides in a syringe for use with a needle within a protective sheath as aforesaid, said syringe comprising a barrel, a nozzle at one end of said barrel, a plunger receivable in the barrel for sliding and sealing movement therealong towards and away from said nozzle, an axial bore provided in the nozzle and extending between the interior of the barrel and the exterior of the syringe, said nozzle being adapted to be received and retained in said socket in the protective sheath whereby said bore in the nozzle provides for fluid communication between the needle and the interior of the barrel.

Preferably, said nozzle is provided with a thread formation for threading engagement with said aperture in the sheath.

In one arrangement, the nozzle may be releasably retained in the socket. In another arrangement the nozzle may be adapted to be fractured to facilitate separation of the protective sheath and the syringe. With the latter arrangement, portion of the nozzle remains captive in the socket of the protective sheath and so obstructs further use of the needle contained within the protective sheath.

Preferably, said nozzle is provided with a weakened section to facilitate fracturing thereof.

In still another form the invention resides in a combination of a syringe and a protective sheath for the needle of the syringe, said syringe comprising a barrel adapted at one end to support said needle with the needle in fluid communication with the interior of the barrel, a plunger receivable in the barrel for sliding and sealing movement therealong towards and away from said one end, said sheath comprising a hollow body mounted on the barrel for movement relative to the barrel between a first position in which the needle is disposed wholly within the confines of the hollow body and a second position in which the needle extends outwardly of the hollow body through an opening in the body.

BRIEF DESCRIPTION OF THE DRAWINGS

The invention will be better understood by reference to the following description of one specific embodiment thereof as shown in the accompanying drawings in which:

FIG. 1 is a schematic side view of a protective sheath for a syringe needle;

FIG. 2 is a schematic side view of a syringe for use with the protective sheath shown in FIG. 1;

FIG. 3 is a view showing the protective sheath and the syringe before the needle contained within the protective sheath is fitted onto the syringe;

FIG. 4 is a view showing the needle within the protective sheath fitted onto the syringe;

FIG. 5 is a schematic side view showing the needle fitted onto the syringe and the protective sheath retracted so as to expose the needle so that an injection fluid can be drawn into the syringe;

FIG. 6 is a schematic side view showing a position of the syringe corresponding to injection of fluid into the body of a patient;

FIG. 7 is a view showing the syringe after completion of the injection and the syringe needle returned into the protective sheath;

FIG. 8 is a view showing the syringe needle isolated within the sheath and the syringe separated from the needle;

DETAILED DESCRIPTION OF THE PREFERRED EMBODIMENTS OF THE INVENTION

Figure 9:
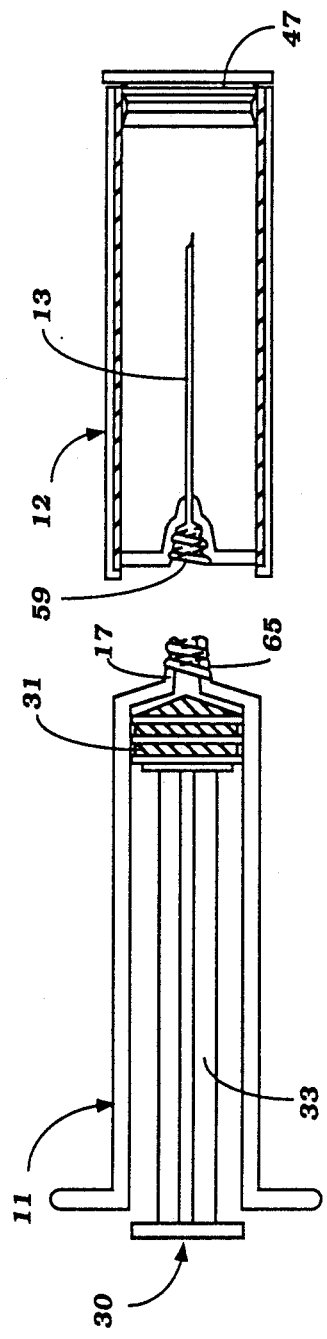
FIG. 9 is a side view of a protective sheath for a needle and a syringe, according to a second embodiment.

The embodiments shown in the drawings are each directed to a combination of a syringe 11 and a protective sheath 12 for a needle 13 for the syringe. The needle is moveable between a position in which it is wholly contained within the protective sheath and a position in which it extends outwardly from within the sheath, as will be explained in more detail later.

In the first embodiment, which is shown in FIGS. 1 to 8 of the accompanying drawings, the syringe 11 comprises a barrel 15 which has a nozzle 17 at its distal end 19 and which is open at its proximal end 21. A flange 23 is formed around the opening at the proximal end of the barrel to provide a means by which a user may grip the barrel while using the syringe. The nozzle 17 defines an axial passage 25 one end of which communicates with interior of the barrel while the other end opens onto the exterior of the barrel. An external thread formation 27 is provided on the nozzle 17.

The syringe further comprises a plunger 30 which includes a piston 31 and a shank 33. The piston is received in the syringe barrel and is in sliding and sealing engagement with the barrel. The shank 33 is connected to the piston 31 and extends out through the opening at the proximal end of the syringe barrel. The outer end of the shank has a flange 35 to facilitate manual operation of the plunger.

The protective sheath 12 comprises a hollow body 41 having a cylindrical side wall 43. The hollow body is provided with an opening 45 at one end which it can be selectively closed by a closure means 47 in the form of a cap. The hollow body is provided with a movable wall 49 which is mounted in the cylindrical side wall for sliding movement therealong. A track means 51 is provided for guiding the movable wall in its movement along the cylindrical side wall. The track means 51 is in the form of a pair of longitudinal ribs provided on diametrally opposed sides of the inner surface of the cylindrical side wall and two recesses (not shown) which are provided in the periphery of the movable wall and each of which receives one of the longitudinal ribs.

The syringe needle 13 is mounted on the movable wall 49 for movement with the wall. The syringe needle has an outer end 55 which is provided with a sharp point for penetrating the body of a patient and an inner end 57 which defines a socket 59 to receive and retain the nozzle 17 of the syringe 11. The socket 59 is formed integral with the movable wall 43 and is provided with an internal thread formation 61 for engagement with the external thread formation 27 on the nozzle. When the nozzle 17 of the syringe is received and retained within the socket 59 at the inner end of the syringe needle, the axial passage 25 in the nozzle is in fluid communication with the axial bore in the needle.

The cylindrical side wall of the sheath is of an internal diameter which is larger than the external diameter of the barrel of the syringe. In this way, the barrel of the syringe can be received in the hollow body as the movable wall is moved in the direction towards the opening 45.

Operation of the syringe will now be described with reference to FIGS. 3 to 8 of the accompanying drawings.

The syringe 11 and the protective sheath 12 with the needle 13 therein, are packaged separately. The sheath 12 maintains the needle in a sterile environment prior to use. When an injection is to be given to a patient, the syringe and the protective sheath are fitted together by screwing the threaded nozzle 17 of the syringe into the socket 59 of the needle, as shown in FIG. 4 of the drawings. The cap 47 is removed from the outer end of the protective sheath to expose the opening 49 and the syringe 11 is moved forwardly relative to the sheath so as to cause the movable wall 49 to travel axially along hollow body 41 towards opening 47. The syringe needle 13 moves with the movable wall 49 and extends outwardly of the hollow body through the opening 45, as shown in FIG. 5. In this position the barrel of the syringe is received within the cylindrical side wall of the hollow body of the protective sheath and the syringe needle is exposed so as to allow the syringe to be used to perform an injection. Injection fluid is then drawn into the syringe and the injection performed. After the injection, the syringe 11 is moved rearwardly relative to the protective sheath so as to withdraw the syringe barrel from within the hollow body of the protective sheath. The movable wall moves away from the opening 45 in the hollow body and so withdraws the needle into the confines of the hollow body, as shown in FIG. 7. When the cap 47 is returned into position on the outer end of the protective sheath, the syringe needle 13 is once again isolated. In this position the syringe needle, which may be contaminated, is not exposed for inadvertent puncturing of the patient or any person handling the syringe. The protective sheath can then be unscrewed from the syringe and discarded.

The first embodiment described does not have provision for deterring further use of the discarded syringe needle. Despite warnings from medical and health authorities, there are instances where syringe needles are reused and so provision to prevent this would be of benefit in combatting transmission of infection. The second embodiment of the invention is constructed with such provision.

Figure 10:
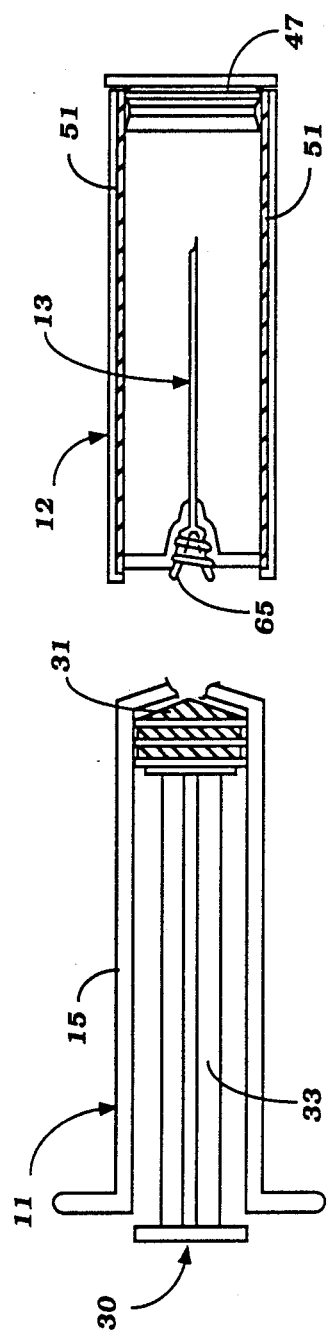
FIG. 10 is a view similar to FIG. 9 showing the syringe and protective sheath after use.

The second embodiment is shown in FIGS. 9 and 10 of the accompanying drawings and is substantially the same as the first embodiment with the exception that a weakened section 63 is provided in the nozzle 17 of the syringe inwardly of the external thread formation 27.

The weakened section 63 is established by the provision of a zone of reduced cross-sectional area in the nozzle. With this arrangement, the protective sheath 12 is not unscrewed from the syringe 11 after completion of the injection but rather the nozzle is fractured at the weakened section to effect such separation. As a result, the portion 65 of the nozzle outwardly of the weakened section remains in the socket 59 of the needle following separation of the nozzle and a protective sheath. The presence of portion 65 of the nozzle in the socket of the syringe needle deters reuse of the syringe needle as it would be necessary to remove the nozzle portion 65 from the socket before a further syringe could be connected to the needle. Additionally, fracturing of the nozzle renders the syringe useless.

It should be appreciated that the scope of the invention is not limited to the scope of the two embodiments described.

We claim:

1. A protective sheath for a syringe needle one end of which needle is adapted for connection to a syringe, said protective sheath comprising a hollow body having a movable wall and an opening opposite said movable wall, removable closure means for selectively closing said opening, said movable wall being adapted to support said syringe needle with said one end exposed to the exterior of the hollow body to facilitate connection to the syringe, said wall being movable between a first position in which the needle is disposed wholly within the confines of the hollow body and a second position in which the needle extends outwardly of the hollow body through said opening when said removable closure is not in place.

2. A protective sheath according to claim 1 wherein said one end of the needle is integral with said movable wall.

3. A protective sheath according to claim 1 wherein said one end of the needle includes socket opening onto the exterior face of the said movable wall, said socket being arranged to receive and retain part of the syringe to provide fluid communication between the needle and the syringe.

4. A protective sheath according to claim 3 wherein said socket is adapted to threadingly engage said part of the syringe to retain said part in the socket.

5. A protective sheath according to claim 1 wherein said hollow body includes side wall means one end of the which defines said opening and wherein said movable wall is slidably supported between said side wall means for movement therealong between said first and second positions.

6. A protective sheath according to claim 5 further comprising guide means for guiding said movable wall as it moves along said side wall means.

7. A syringe for use with a needle within a protective sheath according to claim 1, said syringe comprising a barrel, a nozzle at one end of said barrel, a plunger receivable in the barrel for sliding and sealing movement therealong towards and away from said nozzle, an axial bore provided in the nozzle and extending between the interior of the barrel and the exterior of the syringe, said nozzle being adapted to be received and retained in said socket in the protective sheath whereby said bore in the nozzle provides for fluid communication between the needle and the interior of the barrel.

8. A syringe according to claim 7 wherein said nozzle is provided with a thread formation for threaded engagement with said aperture in the sheath.

9. A syringe according to claim 7 wherein said nozzle is adapted to be fractured to facilitate separation of the syringe from the protective sheath.

10. A syringe according to claim 9 wherein said nozzle is provided with a weakened section to facilitate fracturing thereof.

11. A combination of a syringe and a protective sheath for the needle of the syringe, said syringe comprising a barrel adapted at one end to support said needle with the needle in fluid communication with the interior of the barrel, a plunger receivable in the barrel for sliding and sealing movement there along towards and away from said one end, said sheath comprising a hollow body having side wall means mounted on the barrel for movement relative to the barrel between a first position in which the needle is disposed wholly within the confines of the hollow body and a second position in which the needle extends outwardly of the hollow body through an opening in the body, a moveable wall mounted within said side wall means for reciprocal movement thereby, and supported on the barrel of said syringe and removable closure means closing said opening when said hollow body is in said first position.

12. The combination of claim 11 wherein said hollow body includes a side wall means the interior of which is larger than the exterior of said barrel whereby said side wall means can be received around said barrel when the protective sheath is in said second position.

13. The combination of claim 12 wherein said side wall means comprises a cylindrical side wall.

14. The combination of claim 13 wherein said needle is fixedly mounted on said movable wall for movement therewith.

15. The combination of claim 11 wherein said needle is fixedly mounted on said movable wall and including a socket opening onto the exterior face of said movable wall and wherein said syringe includes a nozzle adapted to be received and retained in said socket to provide for fluid communication between the interior of the barrel and the bore of the syringe needle.

16. The combination of claim 15 wherein said side wall means comprises a cylindrical side wall and said opening is defined by one end of said cylindrical side wall.

* * * * *